United States Patent
Tran (10) Patent No.: US 8,372,098 B2
(45) Date of Patent: Feb. 12, 2013

(54) FLUID LINE REMOVAL DEVICE FOR REMOVING A FLUID LINE FROM A BODY AND RELATED METHODS

(75) Inventor: Tri (Tommy) Tran, Orlando, FL (US)

(73) Assignee: Merit Medical Systems, Inc., South Jordan, UT (US)

( * ) Notice: Subject to any disclaimer, the term of this patent is extended or adjusted under 35 U.S.C. 154(b) by 1440 days.

(21) Appl. No.: 11/672,554

(22) Filed: Feb. 8, 2007

(65) Prior Publication Data

US 2007/0185510 A1    Aug. 9, 2007

Related U.S. Application Data

(60) Provisional application No. 60/771,208, filed on Feb. 8, 2006.

(51) Int. Cl.
*A61B 17/32* (2006.01)

(52) U.S. Cl. .................................. 606/167; 606/108

(58) Field of Classification Search .............. 606/129, 606/108, 136, 110, 159, 190, 167–170; 128/207.15; 604/174
See application file for complete search history.

(56) References Cited

U.S. PATENT DOCUMENTS

| | | | | |
|---|---|---|---|---|
| 3,653,388 A * | 4/1972 | Tenckhoff | ............... | 604/170.01 |
| 4,681,570 A * | 7/1987 | Dalton | ............... | 604/524 |
| 4,955,890 A * | 9/1990 | Yamamoto et al. | ............... | 606/108 |
| 5,071,408 A | 12/1991 | Ahmed | ............... | 606/108 |
| 5,341,816 A * | 8/1994 | Allen | ............... | 600/567 |
| 5,620,451 A | 4/1997 | Rosborough | ............... | 606/108 |
| 5,830,184 A * | 11/1998 | Basta | ............... | 604/104 |
| 5,897,561 A * | 4/1999 | Raines | ............... | 606/108 |
| 6,206,899 B1 | 3/2001 | Ginn | ............... | 606/159 |
| 6,319,265 B1 | 11/2001 | Ginn | ............... | 606/159 |
| 6,361,541 B1 * | 3/2002 | Barnhart | ............... | 606/108 |
| 6,682,535 B2 | 1/2004 | Hoogland | ............... | 606/80 |
| 6,890,308 B2 | 5/2005 | Islam | ............... | 600/564 |
| 6,926,721 B2 | 8/2005 | Basta | ............... | 606/108 |
| 7,107,789 B1 | 9/2006 | Bruner | ............... | 63/15.7 |
| 2002/0032411 A1 | 3/2002 | Basta | ............... | 604/174 |
| 2004/0199110 A1 * | 10/2004 | Basta | ............... | 604/104 |
| 2006/0116691 A1 | 6/2006 | Bonacci | ............... | 606/108 |
| 2006/0129134 A1 | 6/2006 | Kerr | ............... | 604/539 |
| 2006/0264993 A1 * | 11/2006 | Lee | ............... | 606/167 |
| 2007/0118148 A1 * | 5/2007 | Daniele et al. | ............... | 606/108 |

FOREIGN PATENT DOCUMENTS

| | | |
|---|---|---|
| DE | 3006170 | 8/1981 |
| WO | WO0243594 | 6/2002 |
| WO | WO2007062091 | 5/2007 |

* cited by examiner

*Primary Examiner* — Gary Jackson
*Assistant Examiner* — Katrina Stransky
(74) *Attorney, Agent, or Firm* — Stoel Rives LLP (57) ABSTRACT

A fluid line device is for removing a fluid line from a body and may include a handle and a cutting head having a proximal end carried by the handle, and a distal end spaced apart from the proximal end. A fluid line channel may extend through the cutting head between the proximal end and the distal end for receiving the fluid line. The cutting head may also include a guide carried within the fluid line channel for supporting the fluid line therein during manipulation of the handle so that the cutting edge cuts body tissue away from the fluid line for removal thereof from the body.

8 Claims, 10 Drawing Sheets

FLUID LINE REMOVAL DEVICE FOR REMOVING A FLUID LINE FROM A BODY AND RELATED METHODS

CROSS-REFERENCE TO RELATED APPLICATIONS

This application claims the benefit of U.S. Provisional Application No. 60/771,208, filed Feb. 8, 2006, the entire disclosure of which is incorporated by reference herein.

FIELD OF THE INVENTION

The present invention relates to the field of medical devices, and, more particularly, to fluid line removal devices and related methods.

BACKGROUND OF THE INVENTION

For certain medical procedures it is necessary to insert a fluid line into a patient for removing or introducing a fluid. One example of such fluid lines are catheters. Generally speaking, catheters are either used for a relatively short term (e.g., a few hours or days for surgery, etc.), or for more long-term applications. For example, one long-term usage is for hemodialysis for ultra filtration of the blood for patients with renal failure. Another catheter use is for long-term central venous access for prolong intravenous antibiotics, difficult intravenous access, chemotherapy, peritoneal dialysis, or total parenteral nutritional. These catheters are placed via entry points in the internal jugular vein, subclavian vein, femoral veins, or intraperitoneal. The catheters include stabilizing devices to anchor the catheter to the subcutaneous tissues.

One common anchoring device is a tissue ingrowth cuff. The tissue ingrowth cuff seals the opening from within the body and helps stop bleeding and prevent infection. Such a cuff is typically made of Dacron® or a similar biocompatible material, and is attached by an adhesive layer to the outer surface of a catheter cannula. The cuff is generally located on the catheter such that when a distal portion of the catheter is in position in a location to be catheterized, the cuff is positioned external to the catheterized part of the body, but below the surface of the skin in the subcutaneous tissue.

In some cases, the cuff is positioned on the catheter such that when the distal portion of the catheter is inserted in the body part, the cuff is located in a subcutaneous tunnel. The tunnel is formed by a tunneling tool, such as a trocar, either before or after cannulation of the vessel with the distal portion of the catheter. The proximal portion of the catheter having the cuff is drawn in through the tunnel by the tool while the tool passes through the subcutaneous tissue. The cuff is generally sized such that when the procedure is done, the cuff will fit snugly in the tunnel or other area.

After a period of time, the surrounding tissue grows into the fabric of the cuff such that the catheter is stabilized in the catheterized location. In addition, the catheterized location and the subcutaneous tunnel are sealed off, preventing foreign bodies from entering the wound and blood from exiting or pooling around the catheter near the exit site, thereby preventing patient infection. While such fabric cuffs are effective at stabilizing a catheter, they are also difficult to remove.

In order to remove such a cuff from ingrown subcutaneous tissue, such as a tunnel, a practitioner has to detach the cuff by cutting around the cuff with a scalpel or dissecting scissors. The practitioner has to cut the subcutaneous tissue surrounding all edges of the cuff into which tissue has grown. Tissue growth occurs substantially transverse to the longitudinal axis of the cuff around the outer circumference of the cuff. In addition, tissue growth also occurs at angles oblique to the longitudinal axis of the cuff along both of the cuff's side edges. The practitioner must cut around the circumference of the cuff and both side edges to detach the cuff in a relatively difficult, time-consuming surgical procedure that can increase patient bleeding and infection if the whole cuff is not removed. Such prolong surgery and increased bleeding presents several risks, including increased risk of infection. The procedure may also possibly contribute to an increased chance of scar tissue build-up within the subcutaneous area such that patients requiring multiple catheterization procedures may become increasingly difficult to catheterize.

The fabric cuffs also pose problems in the subcutaneous tunneling procedures. Because the cuffs are sized to provide a snug fit in the subcutaneous area, they are difficult to pull smoothly through the tunnel. As the cuff fits snugly within the subcutaneous tunnel, frictional forces against the tunnel wall affect the tunneling and removal of the catheter.

As such, there has been some effort to develop tools to make removal of catheters with tissue ingrowth cuffs easier. One example is set forth in U.S. Patent Application No. 2006/0129134 A1 to Kerr. Kerr is directed to a dialysis catheter assembly, but this reference also discloses a cuff removal tool that has a generally slit tubular structure with a proximal end and a distal end. The proximal end is configured to define a handle and is roughened or knurled to facilitate manipulation and turning of the tool. The distal end defines an array of sharp cutting teeth. The tool is used by telescoping the proximal end of the tube over the catheter. This mounting of the tool over the catheter can be achieved by transversally moving portions of the catheter through the slit defined in the tube. The tool then is rotated so that the teeth cut the scar tissue and the catheter can be removed.

Despite the existence of such tools, further improvements in catheter/fluid line removal devices may be desirable in various applications.

SUMMARY OF THE INVENTION

In view of the foregoing background, it is therefore an object of the present invention to provide a fluid line removal device for removing a fluid line from a body. The device may include a handle and a cutting head having a proximal end carried by the handle and a distal end spaced apart from the proximal end. In one embodiment, the distal end may define a cutting edge. A fluid line channel may extend through the cutting head between the proximal end and the distal end for receiving the fluid line. The cutting head may also include a guide carried within the fluid line channel for supporting the fluid line therein during manipulation of the handle so that the cutting head (or cutting edge) cuts body tissue away from the fluid line for removal thereof from the body.

By way of example, the fluid line may be a catheter having a tissue ingrowth cuff carried thereon. As such, the distal end of the cutting head may have a circumference greater than a circumference of the tissue ingrowth cuff. Additionally, the cutting head may define a slit for inserting the fluid line in the fluid line channel. The cutting head may also be openable to receive the fluid line in the fluid line channel.

More particularly, the guide may be a cross member spanning the fluid line channel. The distal end of the cutting head may be tapered, and the cutting edge of the cutting head may be serrated, for example.

Additionally, the handle of the fluid line removal device may comprise a grip and an extension member connected between the grip and the cutting head, and the extension member may have an arcuate cross section. The extension member may also comprise a plurality of support ribs carried on an interior surface thereof. Further, the extension member may have an open sidewall portion.

A method aspects of the invention is for removing a fluid line from a body. The method may include providing a fluid line removal device that includes a handle and a cutting head having a proximal end carried by the handle, a distal end spaced apart from the proximal end, and a fluid line channel extending through the cutting head between the proximal end and the distal end for receiving the fluid line. The cutting head also includes a guide carried within the fluid line channel. The fluid line is then inserted into the fluid line channel so that the guide supports the fluid line, and the handle is manipulated so that the cutting head cuts body tissue away from the fluid line. After cutting the body tissue, the fluid line is removed from the body.

DETAILED DESCRIPTION OF THE PREFERRED EMBODIMENTS

The present description is made with reference to the accompanying drawings, in which preferred embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements in alternative embodiments.

Referring initially to FIGS. 1-4, a fluid line removal device 40 of the present invention is for use in removing a fluid line 52 from a body 48. In the present embodiment, the fluid line 52 is a catheter with a tissue ingrowth cuff 50 carried thereon. By way of example, the catheter could be a catheter used in kidney dialysis but could also be other types of catheters such as those noted above. In other embodiments, the device 40 could also be used for removing other fluid lines or non-fluid lines, including pacemaker leads and pneumatic drivelines. It will be appreciated by those skilled in the art that the fluid line removal device 40 may be used for removing fluid lines from both human and non-human bodies in different embodiments.

Figure 2:
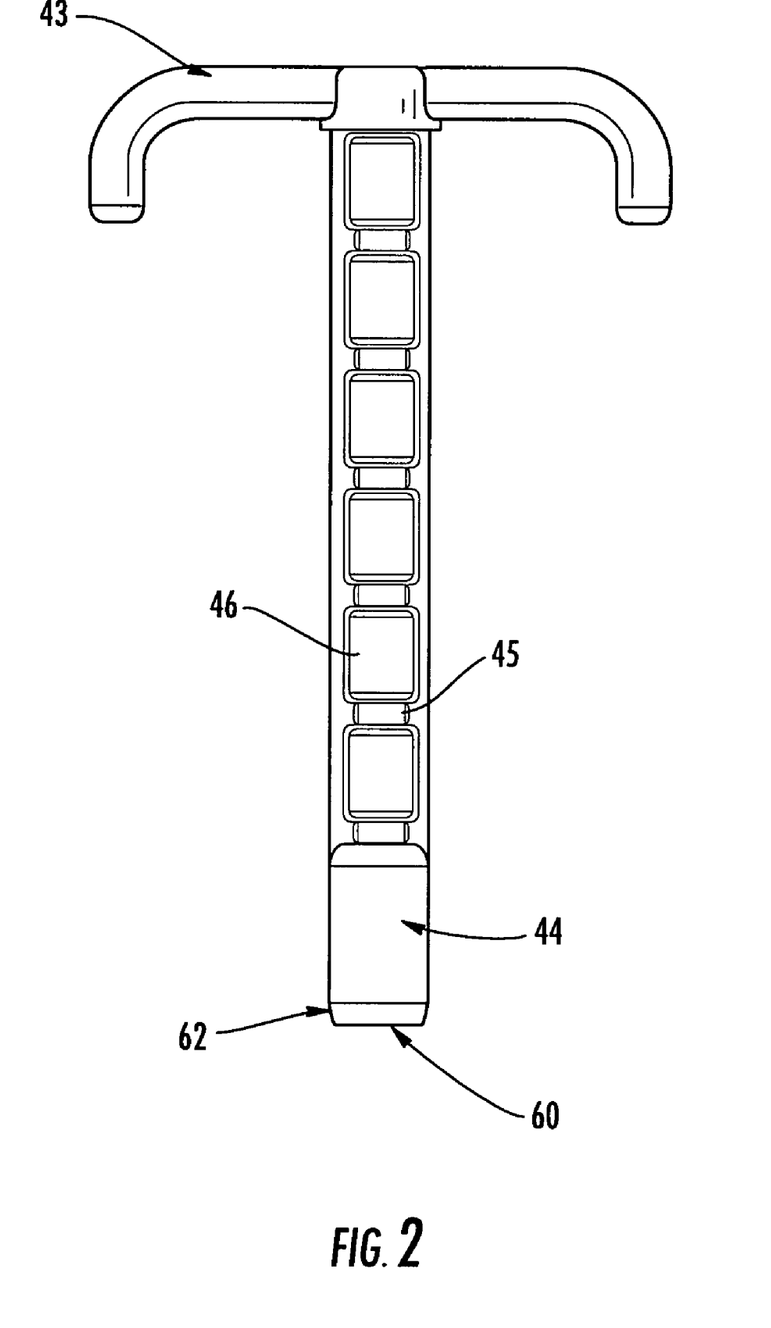
FIG. 2 is a top view of the fluid line removal device of FIG. 1.
Figure 3:
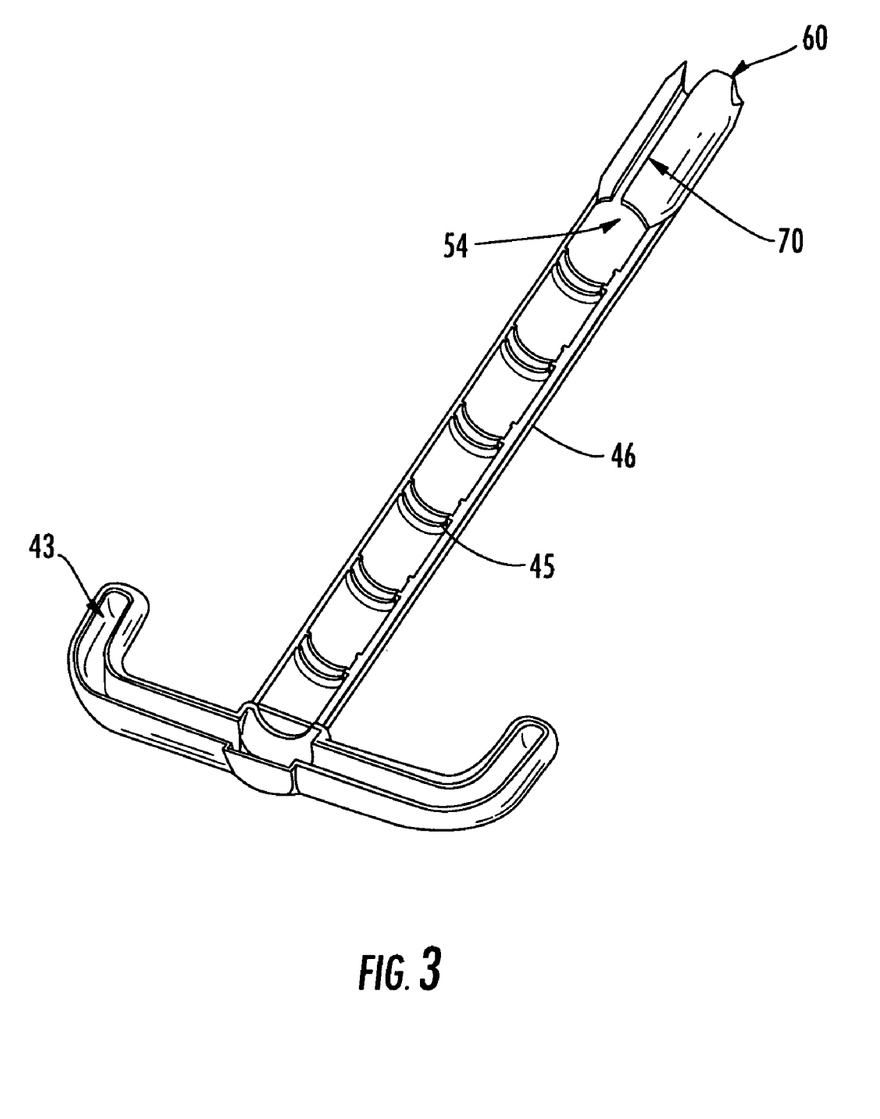
FIG. 3 is a perspective view of the fluid line removal device of FIG. 1.
Figure 4:
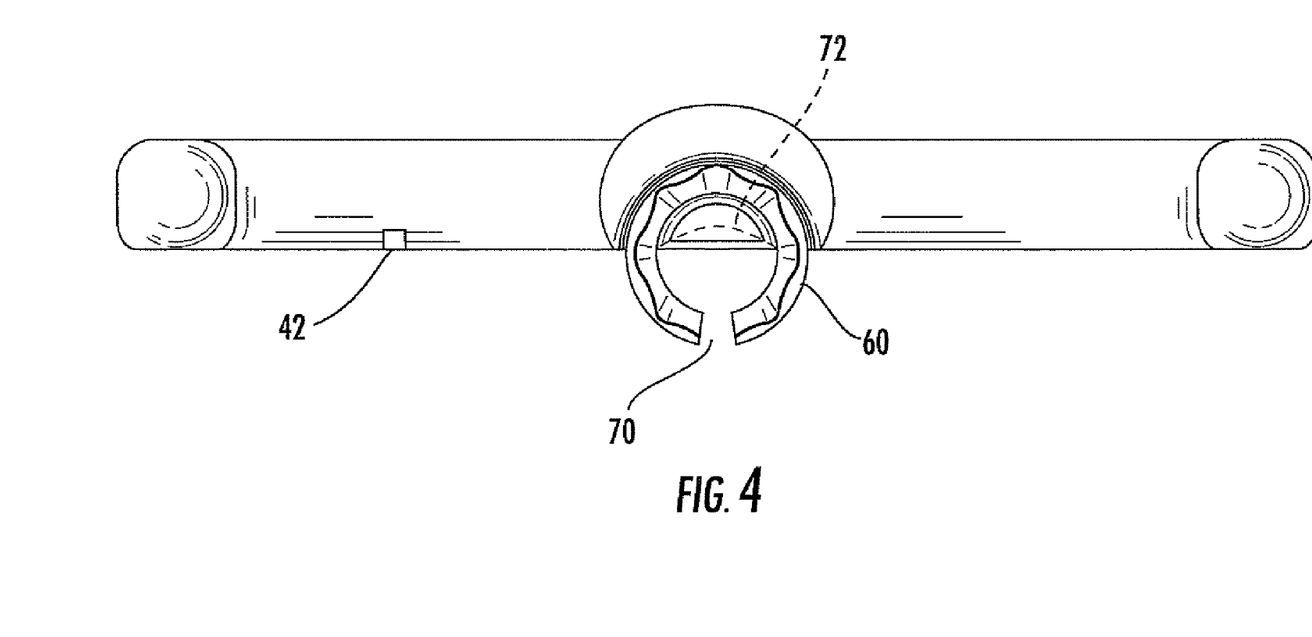
FIG. 4 is an end view of the fluid line removal device of FIG. 1.

The fluid line removal device 40 illustratively includes a handle 42 and a cutting head 44. In the present example, the handle 42 illustratively includes a grip portion 43 and an extension member 46 extending between the grip portion and the cutting head 44. As seen in FIGS. 2 and 3, the grip portion 43 has ends that curve inward toward the cutting head 44 to facilitate gripping by the practitioner. The cutting head 44 has a proximal end 61 (which in the illustrated embodiment is tapered) closest to the handle 42, and a tapered distal end 62 spaced apart from the proximal end and terminating in a cutting edge 60, as shown in FIG. 2.

The tapered distal end 62 of the cutting head allows the fluid line removal device to be inserted into the body 48 and around the fluid line 52 and tissue ingrowth cuff 50, if present, while at the same time pushing the tissue further away from the fluid line using the increasing circumference of the tapered distal end (i.e., like a wedge). In the present example, the cutting edge 60 of the cutting head 44 is serrated, although in other embodiments it may simply be a sharp or thin edge.

The extension member 46 may include a plurality of support ribs 45 carried on the interior surface thereof that provide reinforcement for added strength and durability to help prevent the extension member 46 from breaking during insertion/twisting. The T-shaped grip portion 43 may also advantageously provide stability and directional control of the device 40.

Figure 5:
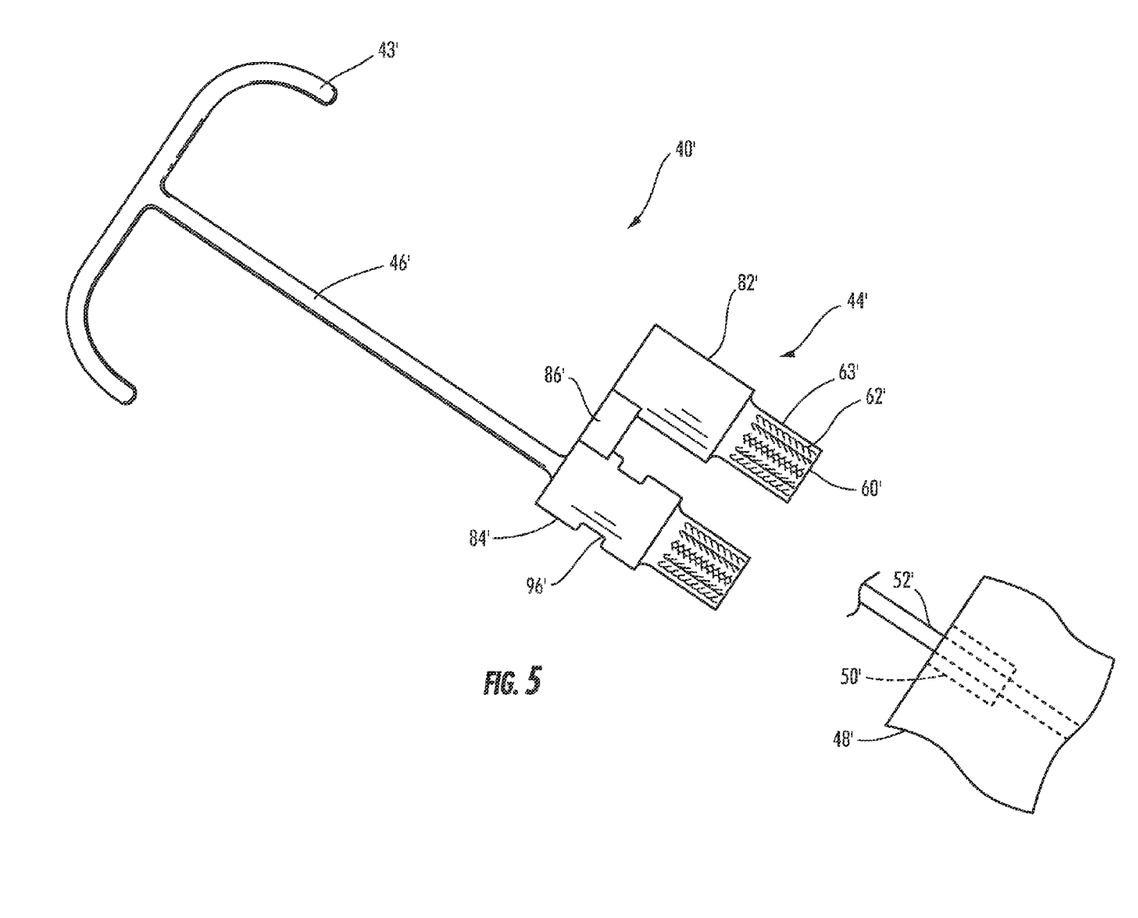
FIG. 5 is a top view of an alternative embodiment of the fluid line removal device of FIG. 1.

The fluid line removal device 40 preferably has a guide carried within the fluid line channel 54 for supporting the fluid line 52 during manipulation of the fluid line removal device. In the present example, the guide is a cross member 72 spanning the fluid line channel 54, as perhaps best seen in FIG. 5. The fluid line 52 rests against the cross member 72, which helps keep the cutting head 44 centered on the fluid line while being inserted into the body 48. In addition to the cross member 72 shown in FIG. 4, the guide may take other shapes, such as a cup-shape, v-shape, curved shape, or other shapes that are suitable to help position and/or maintain the fluid line 52 within the fluid line removal device 40, as will be understood by those skilled in the art.

Figure 1A:
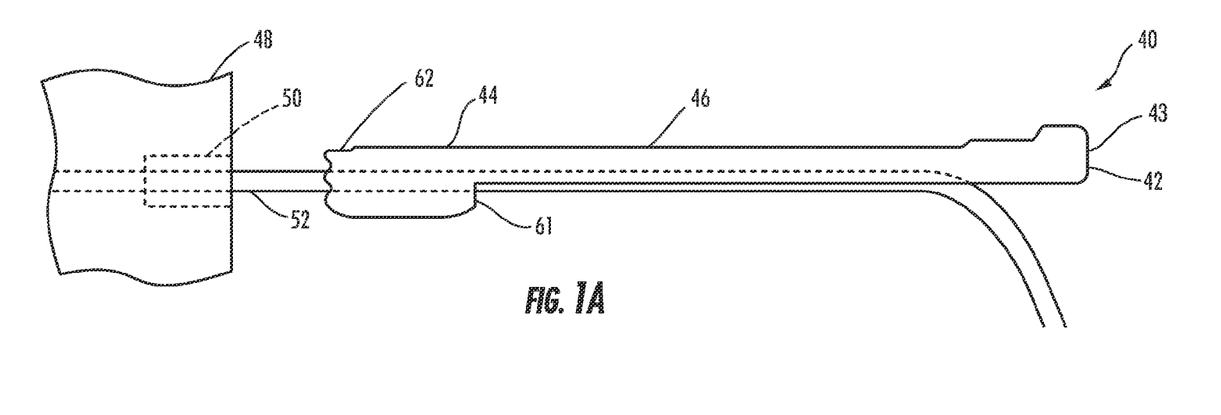
FIGS. 1a and 1b are side views of a fluid line removal device in accordance with the present invention before and during removal of a fluid line from a body, respectively.
Figure 1B:
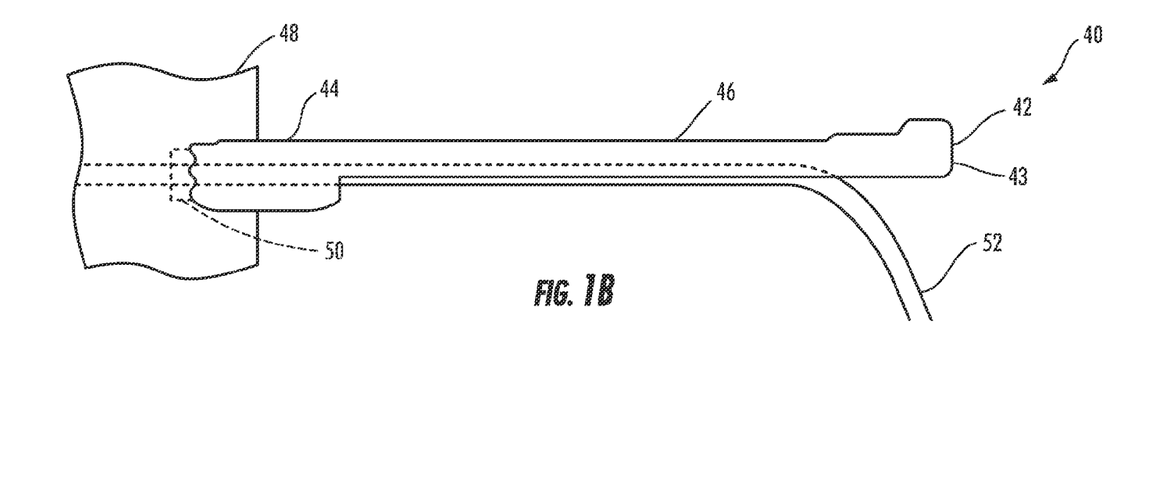

After the fluid line 52 has been inserted into the fluid line channel 54 of the fluid line removal device 40 as shown in FIGS. 1a and 1b, the fluid line removal device is then moved down the fluid line until the distal end 62 of the cutting head 44 makes contact with the exterior surface of the body 48. As noted above, the tissue ingrowth cuff 50 need not be present in all embodiments. Where a tissue ingrowth cuff 50 is present, the distal end 62 of the cutting head 44 preferably has a circumference greater than the tissue ingrowth cuff so that the entire tissue ingrowth cuff can be removed with the fluid line 52, It should be noted that the circumference or shape of the fluid line channel 54 and/or cutting head 44 need not be circular and may be an elliptical or other shape, as will be appreciated by those skilled in the art. Where no tissue ingrowth cuff 50 is present, the cutting head 44 need only have a circumference greater than the circumference of the fluid line 52.

The fluid line removal device 40 is preferably made out of bio-compatible material such as bio-compatible metal or plastic. It is particularly advantageous to construct the fluid line removal device 40 from plastic in embodiments where the device is intended for one use or a very limited number of uses.

As shown in FIG. 1b, the cutting head 44 of the fluid line removal device 40 makes contact with the exterior of the body 50 and is preferably substantially perpendicular to the exterior of the body 48. The fluid line removal device 40 is then manipulated to separate the body tissue from the tissue ingrowth cuff 50, if present, or from the fluid line 52 itself where a tissue ingrowth cuff is not present. This manipulation may be performed in a variety of ways. One approach is to use the serrated edge 60 to cut tissue away from the tissue ingrowth cuff 50 using a rotational movement (i.e., twisting).

The fluid line removal device 40 remains substantially centered on the fluid line 52 but is rotated in a circular motion allowing the teeth of the serrated edge 60 to cut through the tissue surrounding the tissue ingrowth cuff 50 or fluid line 52. The circular motion may involve one or more full 360 degree turns around the fluid line 52 in a clockwise or counter-clockwise direction, and/or back-and-forth rotations through less than 360 degrees around the fluid line 52. Using the circular motion, the teeth of the serrated edge 60 cut the tissue surrounding the tissue ingrowth cuff 50 or fluid line 50 and allows some portion of the cutting head 44 to penetrate into the body tissue and around the tissue ingrowth cuff 50 and fluid line 52 (or the fluid line alone) as shown in FIG. 1b.

As noted above, in other embodiments a consistent sharp edge may be used in place of the serrated edge 60. For such embodiments, user pressure exerted in the direction of the body 48 may be sufficient to separate the body tissue from the tissue ingrowth cuff 50 with less rotation/twisting and still allowing the cutting head 44 to enter the body. Once the cutting head 44 or some portion thereof has penetrated into the body 48 around the tissue ingrowth cuff 50 and fluid line 52 and separated them from the body tissue, the fluid line and the tissue ingrowth cuff, if present, are removed from the body.

There are a number of different embodiments for inserting the fluid line 52 within the fluid line removal device 40. In the present example, the fluid line removal device 40 has a slit 70 running from the distal end 62 to the proximal end 61 of the cutting head 44. The slit 70 is at least slightly greater in width than the diameter of the fluid line 52 to allow the fluid line to be placed in the fluid line channel 54 of the cutting head 44. The slit 70 may also extend through the grip portion 43.

In other embodiments, the cutting head 44 (as well as portions of the extension member 46 and/or grip portion 43) may be completely enclosed around its circumference. In such embodiments, the end of the fluid line 52 furthest from the body is threaded through the fluid line channel 54 of the cutting head 44. The fluid line removal device 40 is then slid down the fluid line 52 until it makes contact with the body 48. The slit 70 may extend beyond the proximal end of the cutting head 44 and through some or the entire portion of the extension member 46 and/or grip portion 43 in embodiments where the extension member and/or grip portion is partially or fully enclosed.

Turning now additionally to FIGS. 5-8, another fluid line removal device 40' is now described which has an openable cutting head 44'. The openable cutting head 44' has a first portion 82' and a second portion 84' that are connected by a tab or hinge 86', which allows the first and second portions to be joined together in closed position around a fluid line, 52'. In an alternative embodiment, the first portion 82' and second portion 84' need not be physically connected by the tab/hinge 86' while in the open state. In this embodiment, one portion remains attached to the handle 42' and the other portion is selectively removable from the attached portion. The fluid line 52' is then positioned in the fluid line channel 54', and the selectively removable portion is then connected to the attached portion to enclose the fluid line 52' within the fluid line channel.

By way of example, the first and second portions 82', 84' of the openable cutting head 44' may be secured in the closed position by slidable tracks or guides. That is, one portion is slid or snapped into the other into a locked position, similar to the way in which a battery cover on a cell phone is moved into a locked position, for example. A number of additional ways of securing the first portion 82' and second portion 84' in a closed position can be used as will be appreciated by those skilled in the art.

Figure 6:
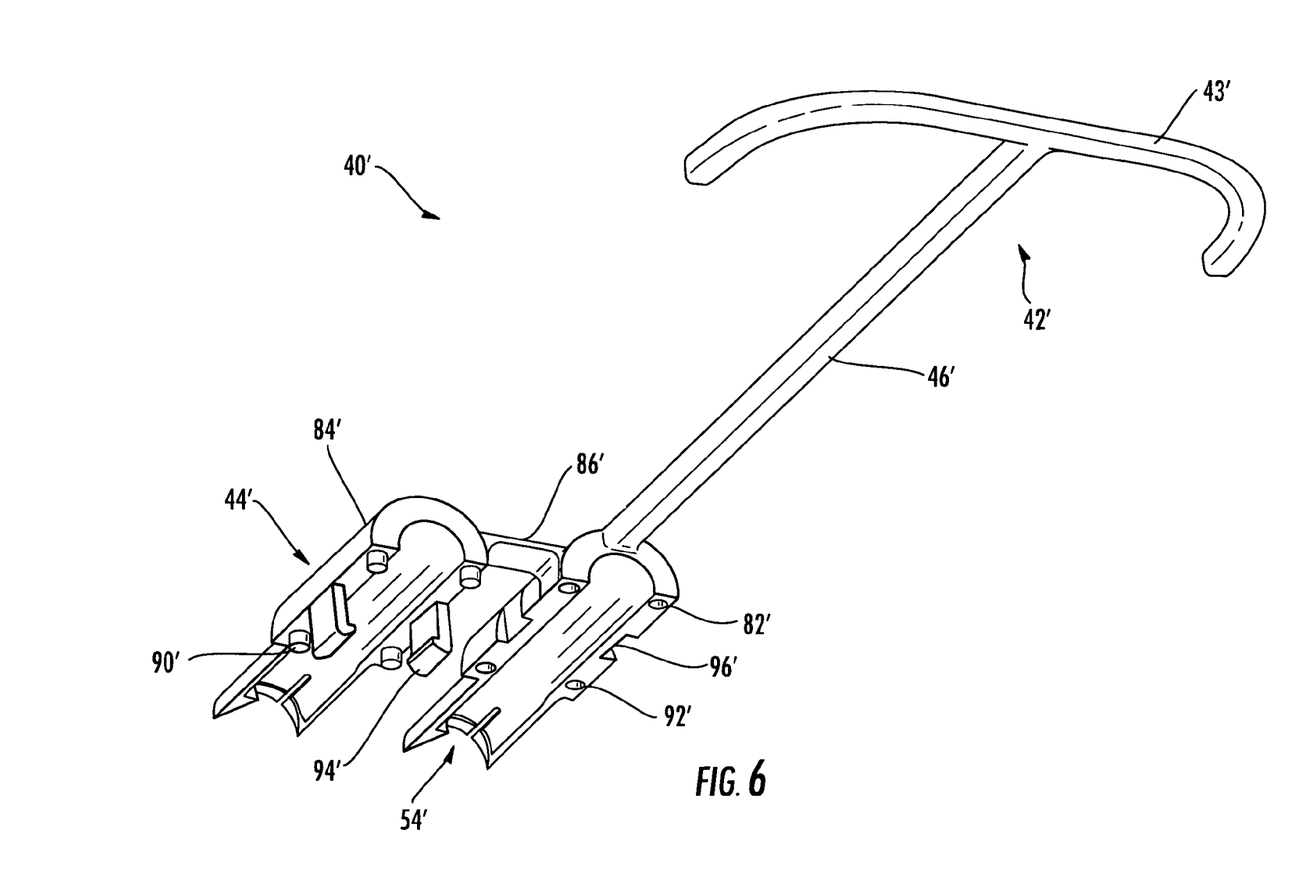
FIG. 6 is a bottom perspective view of the fluid line removal device of FIG. 5.
Figure 7:
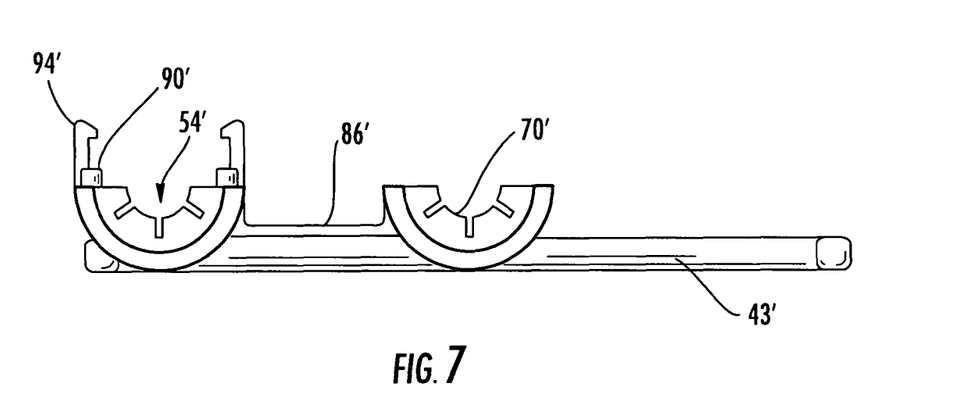
FIG. 7 is an end view of the fluid line removal device of FIG. 5.
Figure 8:
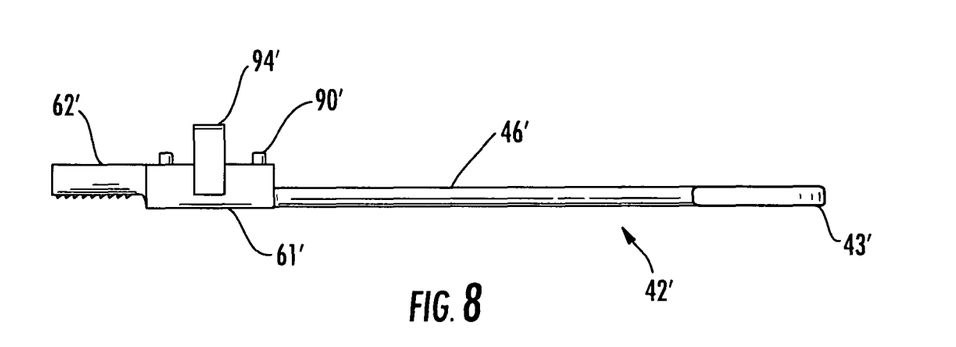
FIG. 8 is a side view of the fluid line removal device of FIG. 5.

The two portions of the openable cutting head 44' may be held in a closed position in a variety of ways. With reference to FIG. 6, clasps 94' and corresponding receiving portions 96' may be used for securing the openable cutting head 44' in the closed position. To further align and/or secure the openable cutting head 44' in the closed position, projections 90' and corresponding holes 92' may be provided at positions along the first member 82' and second member 84'. The pin 90' and hole 92' configuration may in some embodiments be used to secure the first and second portions 82', 84' of the cutting head 44' without the clasps/receiving portions 94', 96' and vice-versa. Of course, other suitable connection mechanisms known to those skilled in the art may also be used.

Another feature of the illustrated fluid line removal device 40' is that the distal end 62' of the cutting head 44' has a serrated cutting surface 63' to further assist in the removal of tissue from a tissue ingrowth cuff 50' (or a fluid line 52' if no tissue ingrowth cuff 50' is present). The serrated cutting surface 63' may be used in addition to, or instead of, a sharp or serrated cutting edge 60'. It should also be noted that serrations may also be present on portions of the proximal end 61' (or even portions of the extension member 46' in some embodiments, if desired). Also in the illustrated embodiment, a guide 70' within the fluid line channel 54' is generally circular and surrounds the fluid line 52' once the fluid line 52' is closed within the fluid line channel 54' (see FIG. 7). Also, in the present example the distal end 62' is not tapered as in the above-described embodiment, although it may also be in some embodiments.

Figure 9:
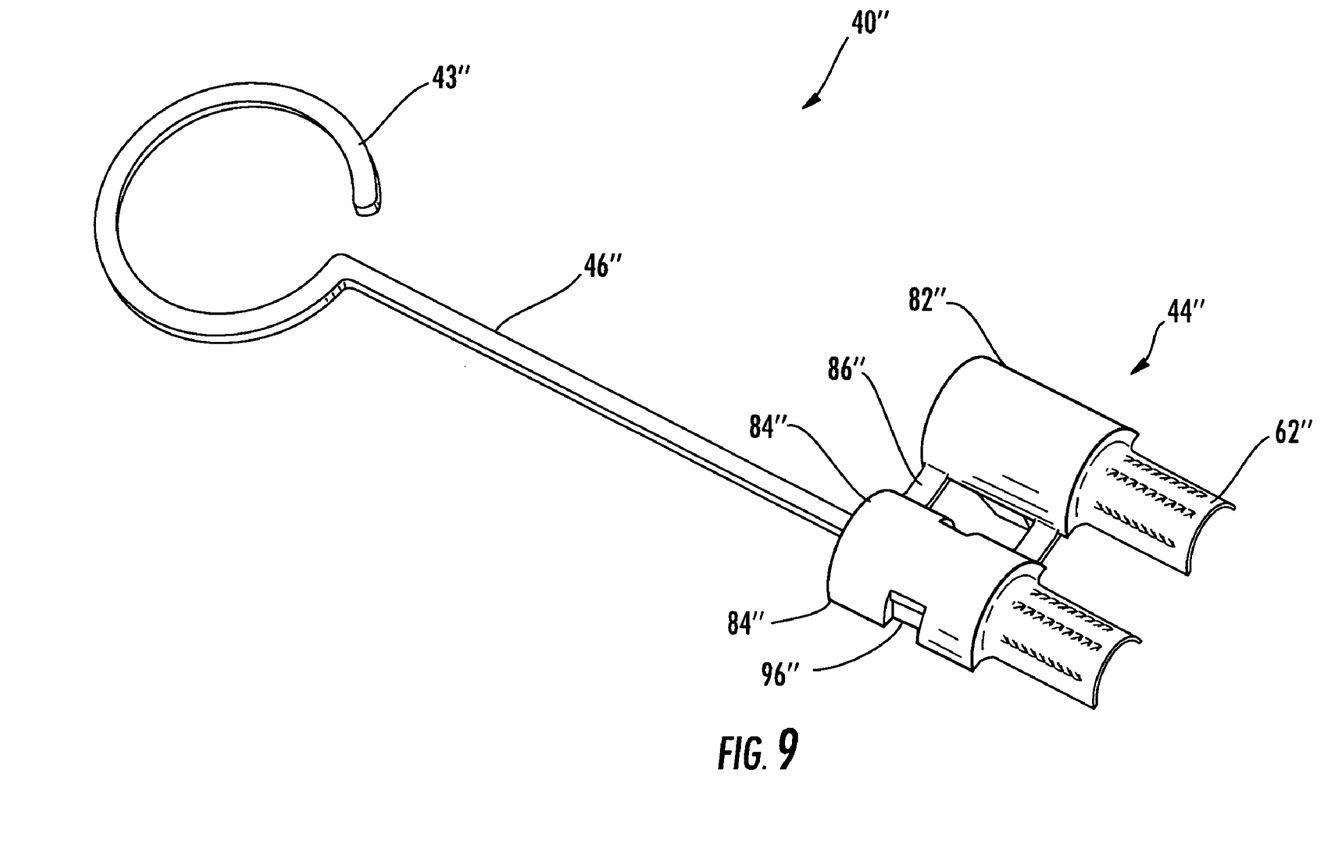
FIG. 9 is a top view of another alternative embodiment of the fluid line removal device of FIG. 1 with the openable cutting head thereof in an open position.
Figure 10:
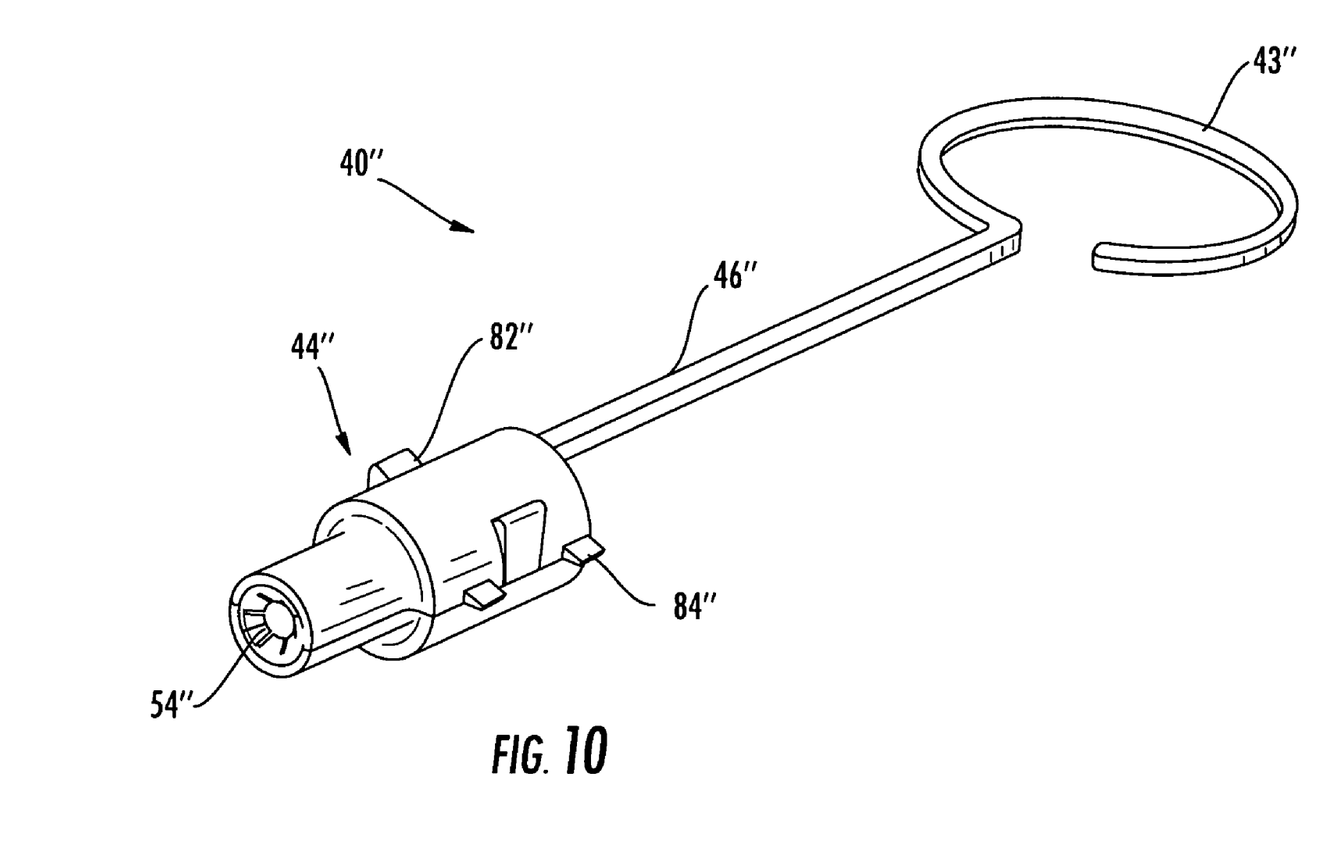
FIG. 10 is a perspective view of the fluid line removal device of FIG. 9 with the openable head in a closed position.
Figure 11:
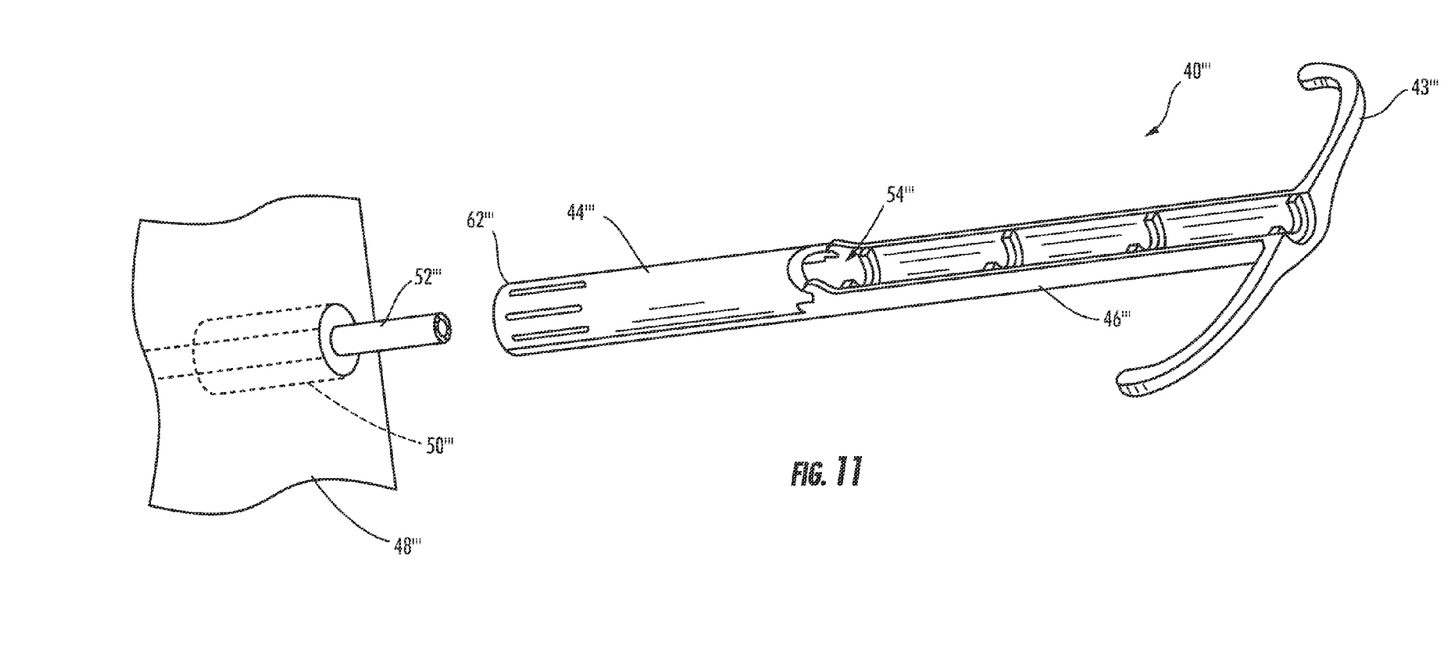
FIG. 11 is a perspective view of still another alternative embodiment of the fluid line removal device of FIG. 1.

In accordance with another embodiment now described with reference to FIGS. 9 and 10, a fluid line removal device 44" includes a generally circular grip portion 43" as opposed to the T-shaped grip portions of the preceding embodiments. Other grip portion shapes may be used to provide desired feel and leverage depending upon user preference and/or the particular procedure to be performed, as will be appreciated by those skilled in the art. Yet another potential embodiment is illustrated in FIG. 11, which includes an elongated cutting head portion 44''' with serrations along the surface thereof, and without a slit therein. Here again, in this embodiment an end of the fluid line 52''' would be inserted into the fluid line channel 54''' at the distal end 62''' of the cutting head 44''', and the device 40''' would then be threaded down the fluid line until reaching the body 48''', as discussed further above.

The various embodiments of the fluid line removal device discussed above may advantageously reduce the procedure time required using traditional incision/suturing techniques, which can be 20-30 minutes, for example, to a fraction of this time. Moreover, use of the fluid line removal device may also advantageously reduce the amount of bleeding and/or risk of infection, as will be appreciated by those skilled in the art. Other advantages may include the relative ease of use, relatively small size, and serrated/sharpened cutting edge which, along with the tapered distal end may advantageously help cut and push tissue away from the ingrowth cuff/fluid line. Also, as noted above, the device 40 may be used for removing catheters and catheter tissue ingrowth cuffs 50, as well as a wide range of other types of fluid lines 52, from human or non-human bodies, as will be appreciated by those skilled in the art.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A method for removing a fluid line from a body comprising:
provideing a fluid line removal device comprising
a handle having a grip portion and a single extension member, and
a cutting head coupled to the single extension member of the handle to cut body tissue away from a fluid line to remove the fluid line from the body, the cutting head having a tubular shape and comprising
a proximal end coupled to a distal end of the extension member of the handle,
a distal end spaced apart from the proximal end, the distal end having an annular cutting edge configured to substantially encircle the fluid line and to cut body tissue away from the fluid line, and
a fluid line channel formed by the tubular shape of the cutting head and having a circumference configured to receive and substantially encircle the fluid line during removal from the body, the fluid line channel extending through the cutting head from the proximal end to the distal end and extending along a longitudinal axis of the cutting head oriented parallel to a longitudinal axis of the extension member, wherein the cutting edge at the distal end of the cutting head defines the distal end of the fluid line channel;
inserting the fluid line in the fluid line channel;
manipulating the handle to rotate the cutting edge about the longitudinal axis of the fluid line channel so that the cutting edge cuts body tissue away from the fluid line; and
removing the fluid line from the body.

2. The method of claim 1, wherein the fluid line comprises a catheter having a tissue ingrowth cuff carried thereon; wherein the distal end has a circumference greater than a circumference of the tissue ingrowth cuff; and wherein manipulating comprises manipulating the handle so that the cutting edge cuts body tissue away from the tissue ingrowth cuff.

3. The method of claim 1, wherein the cutting head defines a slit to access the fluid line channel therein, and wherein inserting comprises inserting the tube in the fluid line channel through the slit.

4. A method for removing a fluid line from a body comprising:
providing a fluid line removal device comprising
a single extension member,
a handle coupled to a proximal end of the extension member,
a cutting head having a tubular shape defining a fluid line channel that extends parallel to a longitudinal axis of the extension member from a proximal end of the cutting head to a distal end of the cutting head, wherein the fluid line channel is configured to receive the fluid line, and
a cutting surface coupled to the distal end of the cutting head, the cutting surface curved and concentric with the fluid line channel of the cutting head and configured to substantially surround the fluid line when the fluid line is received into the fluid line channel and to cut body tissue away from the fluid line for removal of the fluid line from the body;
inserting the fluid line in the fluid line channel;
manipulating the handle so that the cutting head cuts body tissue away from the fluid line; and
removing the fluid line from the body.

5. The method of claim 4, wherein the fluid line comprises a catheter having a tissue ingrowth cuff carried thereon; wherein the distal end has a circumference greater than a circumference of the tissue ingrowth cuff; and wherein manipulating comprises manipulating the handle so that the cutting edge cuts body tissue away from the tissue ingrowth cuff.

6. The method of claim 4, wherein the cutting head defines a slit therein, and wherein inserting comprises inserting the tube into the fluid line channel through the slit.

7. The method of claim 4, wherein said cutting head comprises a first portion coupled to the extension member and a second portion coupled to the first portion by a hinge that allows the second portion to be joined to the first portion in a closed position around the fluid line and to rotate to an open position, wherein rotation of the second portion around on hinge is about an axis that is parallel to the longitudinal axis of the extension member, the method further comprising:
opening the cutting head by rotating the second portion on the hinge to an opened position;
inserting the fluid line into the fluid line channel; and
closing the cutting head by rotating the second portion on the hinge to a closed position.

8. The method of claim 4, wherein manipulating the handle includes rotating the handle about a longitudinal axis of the extension member and thereby rotate the cutting edge around a longitudinal axis of the fluid line channel.

* * * * *